United States Patent [19]

Hunt

[11] 4,093,626

[45] June 6, 1978

[54] β-LACTAM ANTIBIOTICS

[75] Inventor: Eric Hunt, Reigate, England

[73] Assignee: Beecham Group Limited, United Kingdom

[21] Appl. No.: 752,002

[22] Filed: Dec. 20, 1976

[30] Foreign Application Priority Data

Jan. 27, 1976 United Kingdom ............... 02976/76

[51] Int. Cl.² .......................................... C07D 498/04
[52] U.S. Cl. ......................... 260/307 FA; 260/239 A; 424/271; 424/272
[58] Field of Search .................. 260/307 FA; 424/272

[56] References Cited

U.S. PATENT DOCUMENTS 3,334,095   8/1967   Houlihan ............................... 260/244

Primary Examiner—Raymond V. Rush

Attorney, Agent, or Firm—Jacobs & Jacobs

[57] ABSTRACT

Compounds of the formula

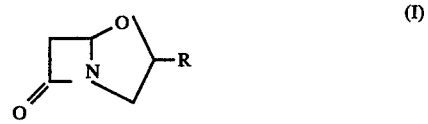

(I)

wherein R is hydrogen, alkyl of 1 to 4 carbon atoms, alkenyl of 2 to 4 carbon atoms, epoxide of 2 to 4 carbon atoms or alkyl of 1 to 4 carbon atoms substituted by 1 or 2 halogen atoms, hydroxyl, etherified or acylated hydroxyl of 1 to 7 carbon atoms, azido, phthaliamido, SR¹, SOR¹ or SO₂R¹ wherein R¹ is aryl, are useful for their β-lactamase inhibitory activity and their antibacterial activity.

5 Claims, No Drawings

β-LACTAM ANTIBIOTICS

The present invention relates to a novel β-lactam containing compounds, to pharmaceutical compositions containing them and to a process for their preparation.

More specifically this invention relates to fused β-lactams which may be used in anti-bacterial compositions by virtue of their moderate anti-bacterial activity and/or their ability to inhibit β-lactamases such as those of Staphylococcal origin.

The present invention provides the compounds of the formula (I):

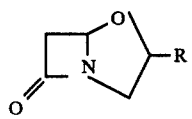
(I)

wherein R is a hydrogen atom, an alkyl group of 1–4 carbon atoms, an alkenyl group of 2–4 carbon atoms, an epoxide group of 2–4 carbon atoms or an alkyl group of 1–4 carbon atoms substituted by one or two groups selected from halogen atoms, hydroxyl, $C_{1-7}$ etherified or acylated hydroxyl, azido, phthalamido, or $SR^1$, $SOR^1$ or $SO_2R^1$ group where $R^1$ is an aryl group [such as an optionally substituted phenyl group (e.g. phenyl or nitrophenyl) or a methyltetrazolyl group].

Certain particularly suitable compounds of the formula (I) include those of the formula (II) or (III):

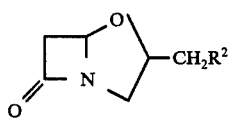
(II)

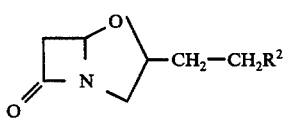
(III)

wherein $R^2$ is a halogen atom or a hydroxyl, $C_{1-7}$ acylated hydroxyl or $SR^3$, $SOR^3$ or $SO_2R^3$ group where $R^3$ is an optionally substituted phenyl group. Preferred groups $R^2$ include the bromine atom or a hydroxy, acetyloxy, propionyloxy, phenylthio, phenylsulphinyl or phenylsulphonyl group.

The compounds of this invention can exist as diastereomers as carbon atoms 3 and 5 are asymmetric centres. In general, the preferred isomer is that in which the hydrogen atom at C(3) is trans to the hydrogen atom at C(5) thus:

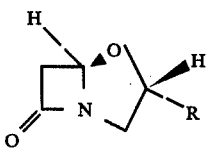

In addition the group R may contain further asymmetric centres, for example when R incorporates a sulphinyl group or a secondary bromide atom or the like. In general there is no preference with respect to the relative configuration at these further asymmetric centres.

In a composition aspect, the present invention provides a pharmaceutical composition which comprises a compound of the formula (I) as hereinbefore described. Such compositions will also comprise a pharmaceutically acceptable carrier.

The composition of this invention will normally be adapted for administration to humans and other mammals, for example, in conventional modes of treatment of diseases of the urinary tract, respiratory system and soft tissues as well as diseases such as otitis media and mastitis and the like.

Suitable forms of the compositions of this invention include tablets, capsules, creams, syrups, suspensions, solutions, reconstitutable powders, and sterile forms suitable for injection or infusion may be used. Such compositions may contain conventional pharmaceutically acceptable materials such as diluents, binders, colours, flavours, preservatives, disintegrants and the like in accordance with conventional pharmaceutical practice.

The compound of formula (I) may be present in the composition as sole therapeutic agent or it may be present together with other therapeutic agents such as a penicillin antibiotic. Thus, suitable penicillin antibiotics for inclusion in the composition of this invention include benzylpenicillin phenoxymethylpenicillin, propicillin, hetacillin, ampicillin. amoxycillin, and in vivo hydrosable esters of compounds such as the acetoxymethyl ester of benzylpenicillin and the pivaloyloxymethyl and phthalidyl ester of ampicillin and amoxycillin.

When present in a pharmaceutical composition together with a penicillin, the ratio of the compound of formula (I) present to penicillin present may be from, for example, 10:1 to 1:3 and advantageously may be from 5:1 to 1:2, for example, 3:1 to 1:1.

The total quantity of antibacterial agents present in any unit dosage form will normally be between 50 and 1500 mg and will usually be between 100 and 1000 mg. However, injectable or infusable compositions may contain greater quantities if desired, for example, 4g or more active material.

Normally between 50 and 6000 mg of the compositions of the invention will be administered each day of treatment but more usually between 500 and 3000 mg of the compositions of the invention will be administered per day. However, for the treatment of severe systemic infections or infections of particularly intransigent organisms, higher doses may be used in accordance with clinical practice.

This invention also provides a process for the preparation of the compounds of the formula (I) which process comprises the base induced cyclisation of a compound of the formula (IV):

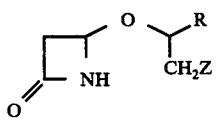
(IV)

wherein Z is a leaving group and R is as defined in relation to formula (I).

Suitable leaving groups Z include chlorine, bromine, iodine, tosyloxy and mesyloxy groups.

The preferred group Z is the bromine atom.

The base used to induce the cyclisation will be one of low nucleophilicity such as potassium carbonate, sodium hydride, 1, 5-diazabicyclo [5,4.0] undec-5-ene or 1, 5-diazabicyclo [4.3.0] nonane.

The cyclisation will normally take place in an inert organic solvent such as diethylether, tetrahydrofuran, dimethyl formamide, 1,2-dimethoxyethane or the like.

The reaction will normally occur at a non-extreme temperature such as −40° to +40° C, for example −20° to +20° C.

The transformation of one group R to another group R is often a useful method of preparing those compounds of the formula (I) which are not conveniently prepared by direct cyclisation of a compound of the formula (IV).

A suitable transformation is shown below in Scheme 1:

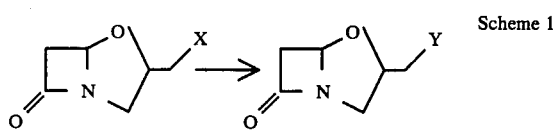

Scheme 1 wherein X is a good leaving group and Y is a nucleophile.

Suitably X is a halogen atom, preferably bromine, chlorine or iodine and Y is a $C_{1-7}$ acyloxy, $C_{1-6}$ alkylthio, azido or arylthio group (such as the phenylthio or nitrophenylthio groups).

Such a transformation will normally be carried out in a water-free organic solvent which will not react with the nucleophilic ion $y^\ominus$.

A further suitable transformation is the oxidation of a substituted thio group to give a substituted sulphinyl group as shown below in Scheme 2:

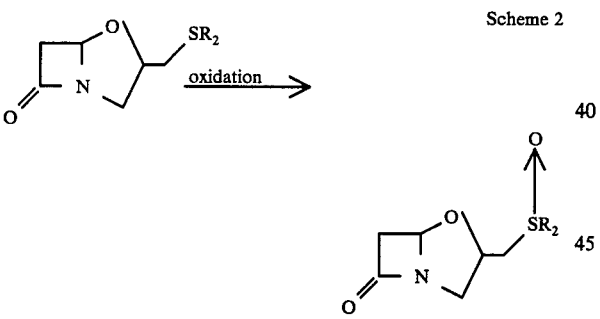

Scheme 2 wherein $R_2$ is as defined in relation to formula (I). The oxidation will be carried out by methods well known to those skilled in the art. Another suitable transformation is the elimination of the elements of $HOSeR^3$ to give a vinylic compound as shown below: Scheme 3:

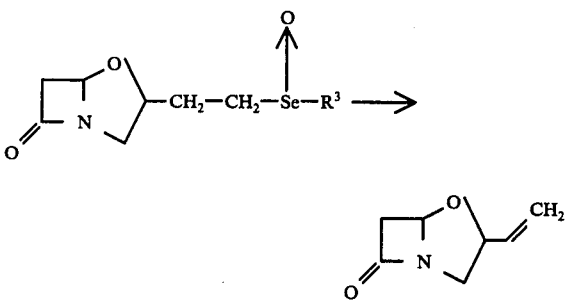

where $R^3$ is an aryl group.

Other suitable transformations include the esterification of hydroxyl group, hydrogenation of benzyloxy groups and other transformations such as those described in the Examples herein.

The following Examples illustrates the invention:

EXAMPLE 1.1

4-(2-Bromoethoxy)azetidin-2-one

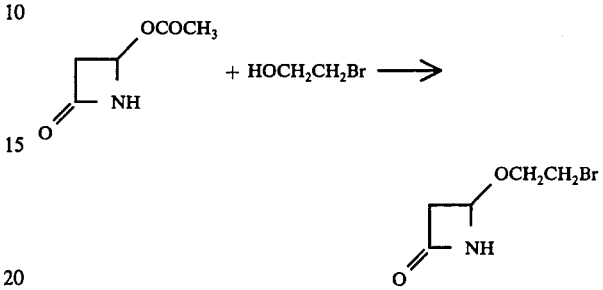

4-Acetoxyazetidin-2-one (10 g) and 2-bromoethanol (10 g) were dissolved together in dry benzene (150 ml) and finely powdered zinc acetate dihydrate (9 g) was added. The mixture was stirred and refluxed with azeotropic removal of water for 24 hours. The mixture was cooled, diluted with ethyl acetate (200 ml), and washed twice with saturated sodium bicarbonate solution and three times with water. The solution was dried (magnesium sulphate) and the solvent removed by evaporation under reduced pressure to yield a pale yellow oil (4.54 g). Chromatography of the oil on silica (50 g) using ethyl acetate/petroleum ether (b.p. 60°-80°) gave the pure title compound as a pale yellow gum (2.6 g, 17%).

$v_{max}$ (CHCl$_3$) : 3390 and 3230 (NH), 1780 ($\beta$-lactam C=O)cm$^{-1}$ $\delta$ p.p.m. (CDCl$_3$) : 3.10 (m, 2H, $\beta$-lactam CH$_2$); 3.60 and 3.95 (both m, both 2H, OCH$_2$CH$_2$Br); 5.27 (dd, J 3Hz, J' 2Hz, 1H, $\beta$-lactam CH); 7.60 (br.s, 1H, NH).

EXAMPLE 1.2

4-Oxa-1-azabicyclo [3.2.0] heptan-7-one

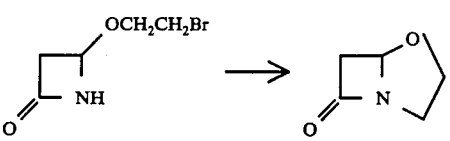

4-(2-Bromoethoxylazetidin-2-one (1.5 g) was dissolved in dry ether (15 ml) and to the stirred solution 1,5-diazabicyclo [5.4.0] undec-5-ene (1.8 g) was added dropwise. The mixture was stirred for 18 hours at room temperature and was then concentrated to ca 5 ml by evaporation of the ether under reduced pressure. The concentrated solution was washed through a column of silica gel (10 g) using 1:2 ethyl acetate/petroleum ether. Evaporation of solvent from the eluent gave the title compound as a colourless oil (270 mg, 31%) which appeared to be homogeneous as judged by t.l.c. and n.m.r. [Found : M$^+$, 113.04764. C$_5$H$_7$NO$_2$ requires 113.04767]

$v_{max}$ (CHCl$_3$) : 1785 ($\beta$-lactam C=O)cm$^{-1}$ $\delta$ p.p.m. (CDCl$_3$) : 2.7 − 3.6 [complex, 3H, $\beta$-lactam CH$_2$ and one C(2)H]; 3.7 − 4.4 [complex, 3H, C(3)H$_2$ and one C(2)H]; 5.25 [d, J 2Hz, 1H, C(5)H]

EXAMPLE 2.1

4-(1,3-Dibromoprop-2-oxy)azetidin-2-one

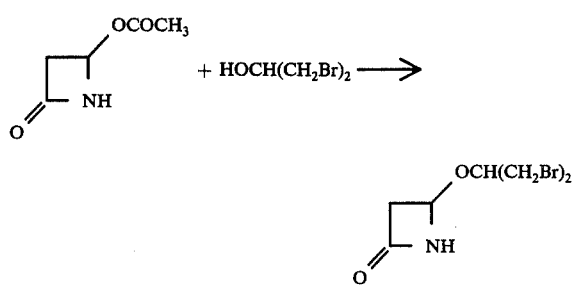

1,3-Dibromopropan-2-ol (6.8 g) and 4-acetoxyazetidin-2-one (6.0 g) were dissolved in dry benzene (100 ml). Zinc acetate dihydrate (3.0 g) was added and the mixture was stirred and refluxed with azeotropic removal of water and acetic acid for 48 hours. Further 4-acetoxyazetidin-2-one (2.0 g) and zinc acetate dihydrate (1.0 g) were added and the reaction was allowed to continue as before for a further 48 hours. The mixture was then cooled and filtered, and the solid was washed with ethyl acetate. The combined filtrate and washings were washed with saturated sodium bicarbonate solution and water. The solution was dried and the solvent removed to yield a yellow gum (6.9 g). Chromatography of the gum on silica gel (70 g) using ethyl acetate/petroleum ether gave the title compound as colourless crystals, m.p. 80°-80.5° (3.9 g, 44%).

[Found : C, 25.30 ; H, 3.01 ; N, 4.51. $C_6H_9Br_2NO_2$ requires C, 25.11 ; H, 3.16 ; N, 4.88%].

$\nu_{max}$ (CHCl$_3$) : 3390 and 3220 (NH), 1780 ($\beta$-lactam C=O)cm$^{-1}$ $\delta$ p.p.m. (CDCl$_3$) : 3.15 (m, 2H, $\beta$-lactam CH$_2$) ; 3.62 (d, J 5Hz, 4H, 2 × CH$_2$Br) ; 3.98 (m, 1H, O-CH) ; 5.38 (dd, J 3Hz, J' 2Hz, 1H $\beta$-lactam CH) ; 7.43 (br. s, 1H, NH).

EXAMPLE 2.2

(3RS, 5RS)- and (3RS, 5SR)-3-Bromomethyl-4-oxa-1-azabicyclo[3.2.0]heptan-7-one

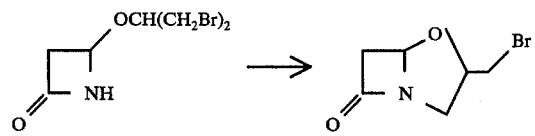

4-(1,3-Dibromoprop-2-oxy)azetidin-2-one (750 mg) was dissolved in dry dimethylformamide (DMF) (5 ml) and anhydrous, finely-powdered potassium carbonate (900 mg) was added. The mixture was stirred at room temperature for 24 hours and was then diluted with ethyl acetate (50 ml). The solution was washed three times with water, dried, and the solvent removed to yield a colourless gum (380 mg). Chromatography of the gum on silica gel (25 g) using ethyl acetate/petroleum ether gave the two isomers of the title compound The (3RS, 5SR)-isomer was obtained as a colourless gum (250 mg, 46%).

$\nu_{max}$ (CHCl$_3$) : 1790 ($\beta$-lactam C=O)cm$^{-1}$ $\delta$ p.p.m. (CDCl$_3$) : 2.7 – 3.4 [complex, 3H, C(6)H$_2$ and C(2)H] ; 3.57 (d, J 6Hz, 2H, CH$_2$Br); 4.17 [dd, J 11.5Hz, J' 6Hz, 1H, C(2)H], 4.68 [quin., J 6Hz, 1H, C(3)H]; 5.52 [d, J 2.5Hz, 1H, C(5) H].

The (3RS, 5RS)-isomer was obtained as a colourless gum (60 mg., 11% yield).

$\nu_{max}$ (CHCl$_3$) : 1790 ($\beta$-lactam C=O)cm$^{-1}$ $\delta$ p.p.m. (CDCl$_3$) : 2.90 [d, J 18Hz, 1H, C(6)H); 3.2 – 3.5 [complex, 2H, C(6)H and C(2)H]; 3.51 (d, J 6Hz, 2H, CH$_2$Br); 3.78 [dd, J 11.5Hz, J' 6Hz, 1H, C(2)H]; 4.65 [quin., J 6Hz, 1H, C(3)H]; 5.35 [d, J 2.0Hz, 1H, C(5)H].

EXAMPLE 3.1

4-(1-Bromobut-3-en-2-oxy)azetidin-2-one

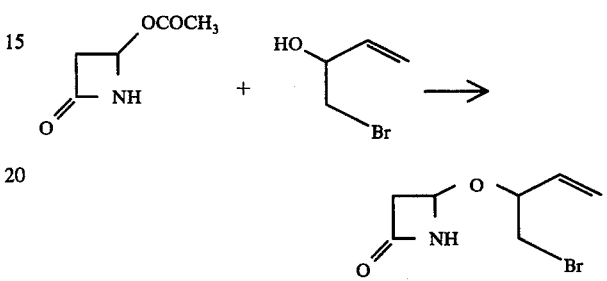

Finely-powdered zinc acetate dihydrate (2.2 g) was suspended in dry benzene and the mixture was stirred and refluxed with azeotropic removal of water until no more water could be removed. 4-Acetoxy azetidin-2-one (3.0 g) and 1-bromobut-3-en-2-ol (3.3 g) were then added and the mixture was stirred and refluxed with exclusion of moisture for 24 hours. Further 4-acetoxyazetidin-2-one (1.0 g) was then added and refluxing was continued for a further 24 hours. The mixture was cooled and filtered and the solid was washed well with ethyl acetate. The combined filtrate and washings were washed with saturated sodium bicarbonate solution and with water. The solution was dried and the solvent removed to yield a yellow gum (4.7 g). The gum was chromatographed on silica gel (30 g) using ethyl acetate/petroleum ether to give the title compound as a colourless gum (3.0 g, 62%).

$\nu_{max}$ (CHCl$_3$) : 3380, 3210 (NH), 1780 ($\beta$-lactam C=O)cm$^{-1}$ $\delta$ p.p.m. (CDCl$_3$) : 3.05 (m, 2H, $\beta$-lactam CH$_2$); 3.45 (d, J 6Hz, 2H, CH$_2$Br); 4.19 (q, J 6Hz, 1H, O-CH); 5.2 – 6.2 (complex, 4H, $\beta$-lactam CH and CH==CH$_2$); 7.3 (br.s, 1H, NH).

EXAMPLE 3.2

4-(1-Bromo-3,4-epoxybut-2-oxy)azetidin-2-one

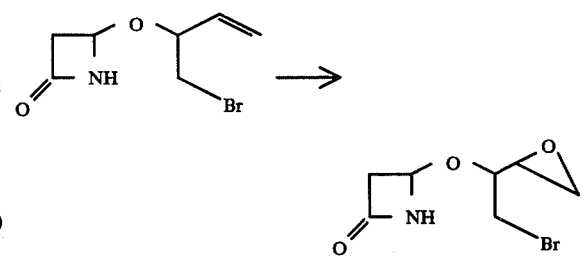

4-(1-Bromobut-3-en-2-oxy)azetidin-2-one (440 mg) was dissolved in dry benzene (5 ml) and m-chloroperbenzoic acid (400 mg) was added. The mixture was refluxed with exclusion of moisture for 24 hours. The solution was cooled, diluted with ethyl acetate (30 ml) and washed with saturated sodium bicarbonate and with water. The solution was dried and the solvent removed to yield a pale gum (420 mg). Chromatography of the gum on silica gel (25 g) using ethyl acetate/petroleum ether gave the title compound as a colourless gum (225 mg, 48%).

$v_{max}$ (CHCl$_3$) : 3370 and 3210 (NH) 1780($\beta$-lactam C=O)cm$^{-1}$ $\delta$ p.p.m. (CDCl$_3$) : 2.7 – 3.7 (complex, 7H, $\beta$-lactam CH$_2$, CH$_2$Br,

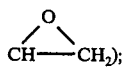

3.85 (m, 1H, O-CH); 5.3 (m, 1H, $\beta$-lactam CH), 7.2 (br.s, 1H, NH).

EXAMPLE 3.3

3-Epoxyethyl-4-oxa-1-azabicyclo [3.2.0]heptan-7-one

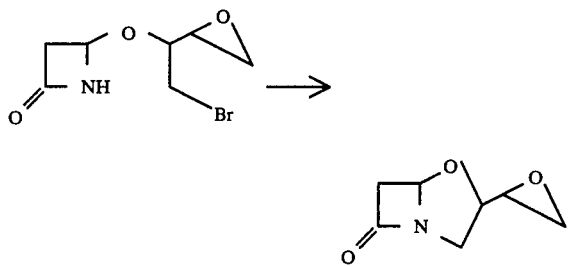

4-(1-Bromo-3,4-epoxybut-2-oxy)azetidin-2-one (200 mg) was dissolved in dry dimethylformamide (DMF) (2 ml) and anhydrous, finely-powdered potassium carbonate (250 mg) was added. The mixture was stirred at room temperature for 24 hours with the exclusion of moisture. The mixture was then diluted with ethyl acetate (30 ml) and was washed with water three times. The solution was dried and the solvent removed to yield a colourless gum (150 mg). Chromatography of the gum on silica gel (20 g) using ethyl acetate/petroleum ether gave the title compound (mixture of isomers) as a colourless gum (36 mg, 28%).

$v_{max}$ (CHCl$_3$) : 1785 ($\beta$-lactam C=O)cm$^{-1}$ $\delta$ p.p.m. (CDCl$_3$) : 2.6 – 4.6 (complex, 8H); 5.40 [m, 1H, C(5)H].

EXAMPLE 4

(3RS, 5RS)- and (3RS, 5SR)-3-(1,2-Dibromoethyl)-4-oxa-1-azabicyclo[3.2.0]-heptan-7-one

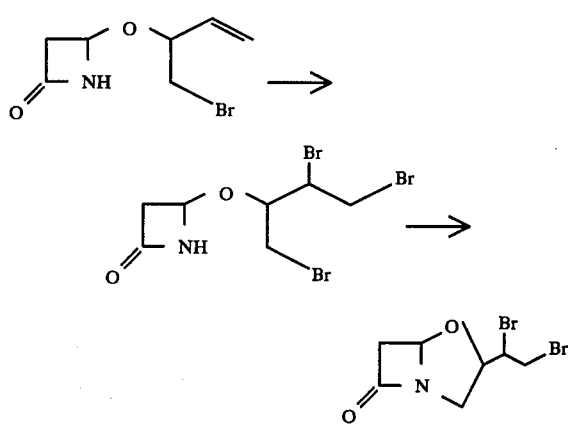

4-(1-Bromobut-3-en-2-oxy)azetidin-2-one (240 mg., 1.1mmole) was dissolved in dry methylene chloride (5 ml) and the solution was stirred and ice-cooled with exclusion of moisture while bromine (175 mg., 1.1mmole) in carbon tetrachloride (1.1 ml) was added dropwise over 10 minutes. After addition was complete, the mixture was stirred and ice-cooled for a further 10 minutes and then the solvent was evaporated under reduced pressure to give the tribromide as a yellow gum (420 gm)

$v_{max}$ (CHCl$_3$) : 3400 and 3250 ($\beta$-lactam NH), 1780 ($\beta$-lactam C=O)cm$^{-1}$ The tribromide was dissolved in dry dimethylformamide (5 ml) and anhydrous finely-powdered potassium carbonate (250 mg) was added to the solution which was then stirred with exclusion of moisture for 2 days. The mixture was diluted with ethyl acetate (50 ml) and washed with water three times (20 ml portions). The solution was dried (magnesium sulphate) and the solvent was removed by evaporation under reduced pressure to give a yellow gum (220 mg). The gum was chromatographed on silica gel (10 g) using 1:5 ethyl acetate/petroleum ether (b.p. 60° – 80°) to give, in order of elution, (3 RS, 5 SR)-3-(1,2-dibromoethyl)-4-oxa-1-azabicyclo[3.2.0]heptan-7-one as a colourless gum (7 mg) and (3 RS, 5RS)-3-(1,2-dibromoethyl)-4-oxa-1-azabicyclo[3.2.0]heptan-7-one as a colourless gum (6 mg).

The (3RS, 5SR)-isomer had $v_{max}$(CHCl$_3$) : 1787 ($\beta$-lactam C=O)cm$^{-1}$; m/e : 273 (M$^+$ —CO, 56%), 271 (M$^+$ —CO, 100%), 269 (M$^+$ —CO, 55%), 260 (15), 258 (33), 256 (21), 254 (3), 220 (15), 218 (15), 192 (79), 190 (79), 178 (18), 176 (18), 164 (9), 162 (9), 150 (9), 149 (15), 148 (9), 135 (42), 133 (42), 112 (24), 70 (67).

The (3-RS, 5-RS)-isomer had $v_{max}$ (CHCl$_3$) : 1785 ($\beta$-lactam C=O)cm$^{-1}$ m/e : 273 (M$^+$ —CO, 50%), 271 (M$^+$ —CO, 100%), 269 (M+ —CO, 50%), 260 (12), 258 (32), 256 (31), 254 (10), 192 (100), 190 (100), 178 (12), 176 (25), 174 (12), 164 (10), 162 (10), 149 (38), 135 (37), 133 (37).

EXAMPLE 5.1

4-(1-Benzyloxy-3-chloroprop-2-oxy)azetidin-2-one

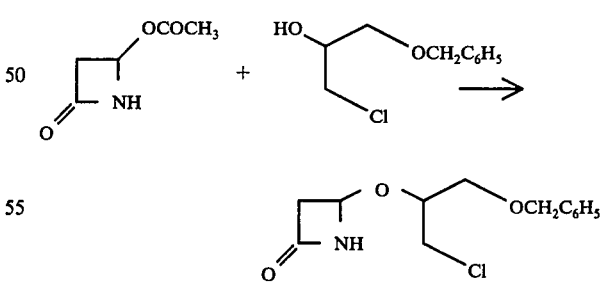

1-Benzyloxy-3-chloropropan-2-ol (10.0 g) was converted into the title compound using the process described in Example 2.1. The title compound was obtained as a pale yellow gum (7.9 g., 58% yield). $v_{max}$ (CHCl$_3$) : 3380 and 3200 (NH), 1775 ($\beta$-lactam C=O)cm$^{-1}$. $\delta$ p.p.m. (CDCl$_3$) 2.7 – 3.3 (m, 2H, $\beta$-lactam CH$_2$), 3.5 – 4.0 (complex, 5H, CH$_2$Cl, OCH, CH$_2$O), 4.49 (s, 2H, OCH$_2$Ph), 5.17 (m, 1H, $\beta$-lactam CH), 7.00 (br.s, 1H, NH), 7.30 (s, 5H, C$_6$H$_5$).

EXAMPLE 5.2

(3RS, 5RS)- and (3RS, 5SR)-3-Benzyloxymethyl-4-oxa-1-azabicyclo[3.2.0]heptan-7-one

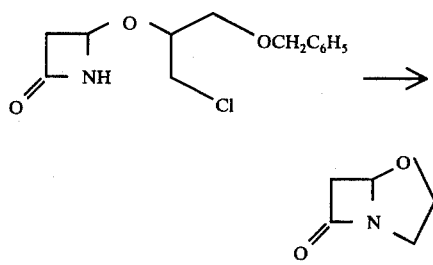

4-(1-Benzyloxy-3-chloroprop-2-oxy)azetidin-2-one (2.2 g., 8.1mmole) was dissolved in dry dimethylformamide (25 ml) and anhydrous finely-powdered potassium carbonate (1.2 g) and potassium iodide (120 mg) were added to the solution. The mixture was stirred at 60° to 70° (bath temperature) with exclusion of moisture for 20 hours. The mixture was cooled, diluted with ethyl acetate (200 ml), and washed three times with water (50 ml. portions). The solution was dried and the solvent was removed to yield a yellow gum (1.1 g). The gum was chromatographed on silica gel (30 g) using ethyl acetate/petroleum ether (b.p. 60°-80°) to give, in order of elution, (3RS, 5SR)-3-benzyloxymethyl-4-oxa-1-azabicyclo[3.2.0]heptan-7-one as a colourless oil (270 mg., 14% yield) and (3RS, 5RS)-3-benzyloxymethyl-4-oxa-1-azabicyclo[3.2.0]-heptan-7-one as a colourless oil (150 mg., 8% yield). Ar-H).

The (3RS, 5SR)-isomer had the following physical characteristics. (Found : M+, 233.10515. $C_{13}H_{15}NO_3$ requires 233.10586). $v_{max}$ (CHCl$_3$) : 1785 ($\beta$-lactam C=O)cm$^{-1}$. $\delta$ p.p.m. (CDCl$_3$): 2.70 (d, J 16Hz, 1H, C(6)H), 2.86 (dd, J 11Hz, J' 6Hz, C(2)H), 3.20 (dd, J 16Hz, J' 2Hz, 1H, C(6)H), 3.49 (d, J 4Hz, 2H, CH$_2$O), 3.85 (dd, J 11Hz, J' 6.5Hz, 1E C(2)H), 4.1-4.55 (overlapped m, 1H, C(3)H), 4.45 (s, 2H, OCH$_2$Ph), 5.35 (d, J 2Hz, 1H, C(5)H), 7.72 (s, 5H, Ar-H). m/e : 233 (M+, 5%), 205 (25), 132 (8), 112 (16), 91(100).

The (3RS, 5RS)-isomer had the following physical characteristics. (Found : M+, 233.10493. $C_{13}H_{15}NO_3$ required 233.10586). $v_{max}$ (CHCl$_3$: 1785 ($\beta$-lactam C=O)cm$^{-1}$. $\delta$ p.p.m. (CDCl$_3$) : 2.6 – 3.3 (complex, 3H, C(6)H$_2$, C(2)H), 3.43 (d, J 4.5Hz, 2H, CH$_2$O), 3.35 – 3.70 (overlapped m, 1H, C(2)H),4.2-4.46 (overlapped m, 1H, C(3)H), 4.46 (s, 2H, OCH$_2$Ph), 5.20 (d, J 2.5Hz, 1H C(5)H, 7.32 (s, 5H, Ar-H). m/e : 233 (M+, 5%), 205 (20), 172 (5), 112 (15), 91(100).

EXAMPLE 6.1

4-(1,4-Dibromobut-2-oxy)azetidin-2-one

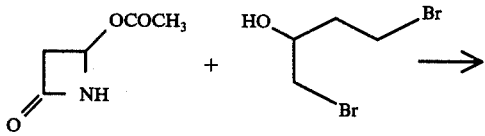

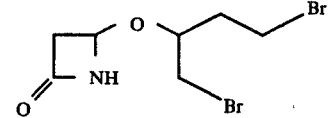

1,4-Dibromobutan-2-ol (12.0 g) was converted into the title compound using the process described in Example 2.1. The title compound was obtained as a pale yellow oil (8.75 g). $v_{max}$ (CHCl$_3$) : 1780 ($\beta$-lactam C=O)cm$^{-1}$. $\delta$ p.p.m. (CDCl$_3$) : 2.15 (m, 2H, CH$_2$), 2.7 — 3.1 (m, 2H, $\beta$-lactam CH$_2$), 3.42 (d, J 5Hz, 2H, CH$_2$Br), 3.4 – 3.6 (m, 2H, CH$_2$Br), 3.82 (quin., J 5 Hz, 1H OCH), 5.25 (m, 1H $\beta$-lactam CH), 7.15 (br.s. 1H, NH).

EXAMPLE 6.2

(3RS, 5RS)- and (3RS, 5SR)-3-(2-Bromoethyl)-4-oxa-1-azabicyclo[3.2.0]heptan-7-one

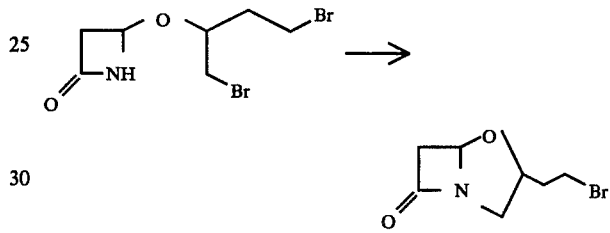

4-(1,4-Dibromobut-2-oxy)azetidin-2-one (4.0 g) was converted into the title compounds using the process described in Example 2.2. A mixture of the two title compounds was obtained as a colourless gum (1.06 g., 36% yield) after chromatography on silica gel. $v_{max}$ (CHCl$_3$) 1787 ($\beta$-lactam C=O)cm$^{-1}$. $\delta$ p.p.m. (CDCl$_3$) : 1.90 – 2.25 (m, 2H, CH$_2$), 2.4 – 3.5 (complex, ca 5H, C(6)H, C(2)H, CH$_2$Br), 3.91 (dd, J 11, J' 6Hz, 0.65H, C(2)H for major isomer), 4.35 (m, 1H, C(3)H), 5.09 (d, J 2Hz, 0.35H, C(5)H for minor isomer), 5.28 (d, J 2Hz, 0.65H, C(5)H for major isomer).

EXAMPLE 7

(3RS, 5SR)-3-Phenylthiomethyl-4-oxa-1-azabicyclo[3.2.0]-heptan-7-one

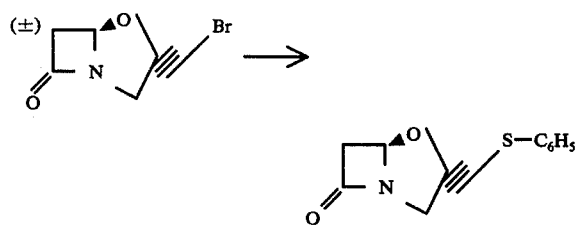

(3RS, 5SR)-3-Bromomethyl-4-oxa-1-azabicyclo[3.2.0]heptan-7-one (210 mg, 1.0 mmole) in dry dimethylformamide (2 ml) was added dropwise to a stirred solution of sodium thiophenolate (1.2 mmole) in dry DMF (5 ml). The solution was stirred at room temperature with exclusion of moisture for 16 hours and was then diluted with ethyl acetate (30 ml). The solution was washed three times with water, dried, and the solvent removed to give a colourless oil. The oil was chromatographed on silica gel (15 g) using ethyl acetate/petroleum ether to give the title compound as a colourless gum (205 mg, 87%). (Found : M+, 235.06551. $C_{12}H_{13}NO_2S$ requires 235.06669. $\nu_{max}$ (CHCl$_3$) 1785 (β-lactam C=O)cm$^{-1}$ δ p.p.m. (CDCl$_3$) 2.6 – 3.5 [complex, 5H, C(6)H$_2$, C(2)H, CH$_2$SPh[; 4.10 [dd, J 11.5Hz, J' 6Hz, 1H, C(2)H]; 4.52 [quin., J 6Hz, 1H, C(3)H]; 5.43 [d, J 2.5Hz, 1H, C(5)H]; 7.48 (5H, aromatic H). m/e : 235 (M+, 100%), 192 (30), 123 (71).

EXAMPLES 8 – 17

The compounds described below were prepared using processes analogues to that described in Example 7. The reaction conditions are summarised in the following Table.

EXAMPLE 9

(3RS, 5SR)-3-p-Nitrophenylthiomethyl-4-oxa-1-azabicyclo[3.2.0]heptan-7-one

Pale yellow gum. (Found : M+, 280.05177. $C_{12}H_{12}N_2O_4S$ requires 280.05177). $\nu_{max}$ (CHCl$_3$) : 1780 (β-lactam C=O), 1510 and 1330 (aromatic NO$_2$)cm$^{-1}$ δ p.p.m. (CDCl$_3$) : 2.71 (d, J 16Hz, 1H, C(6)H), 2.84 (dd, J 11, J' 5Hz, 1H, C(2)H), 3.20 (d, J 5Hz, 2H, CH$_2$S), 3.25 (dd, J 16, J' 2Hz, 1H, C(6)H), 3.92 (dd, J 11, J' 5.5Hz, 1H, C(2)H), 4.38 (quin., J 5Hz, 1H C(3)H), 5.30 (d, J 2H, 1H, C(5)H), 7.35 (d, J 8Hz, 2H, Ar-H), 8.04 (d, J 8Hz, 2H, Ar-H). m/e : 280 (M+, 54%), 238 (44), 169 (22), 168 (22), 152 (17), 112 (67), 84 (45), 70 (100).

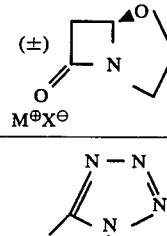

| Example | M⊕X⊖ | Solvent, temperature, time | Yield (%) |
|---|---|---|---|
| 8 | 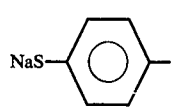 | DMF, 25°, 18 hours | 43 |
| 9 | 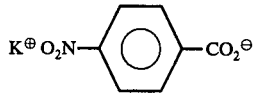 | DMF, 25°, 18 hours (Nitrogen atmosphere) | 72 |
| 10 | KI | DMF, 25°, 5 days | 65 |
| 11 | K⊕ CH$_3$CO$_2$⊖ | DMF, 25°, 7 days | 67 |
| 12 | K⊕ HCO$_2$⊖ | DMF, 75°, 3 days | 38 |
| 13 | Na⊕ C$_6$H$_5$CO$_2$⊖ | DMF, 70°, 4 days | 25 |
| 14 | 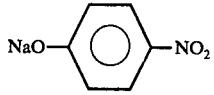 | HMPA, 25°, 66 hours | 64 |
| 15 | 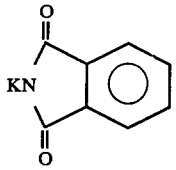 | DMF, 70°, 17 hours | 18 |
| 16 |  | DMF, 25°, 42 hours | 43 |
| 17 | NaN$_3$ | DMF, 25°, 40 hours | 95 |

(DMF = dimethylformamide. HMPA = hexamethylphosphoramide)

EXAMPLE 8

(3RS, 5SR)-3-(1-Methyl-1,2,3,4-tetrazoline-5-thiomethyl)-4-oxa-1-azabicyclo[3.2.0]heptan-7-one Colourless gum. $\nu_{max}$ (CHCl$_3$) : 1785 (β-lactam C=O)cm$^{-1}$. δ p.p.m. (CDCl$_3$) : 2.90 (d, J 17Hz, 1H, C(6)H, ca 2.9 (overlapped m, 1H, C(2)H), 3.47 (dd, J 17Hz, J' 2.5Hz, 1H, C(6)H), 3.67 (d, J 6Hz, 2H, SCH$_2$), 4.03 (s, 3H, NCH$_3$), 4.18 (dd, J 11.5Hz, J' 6Hz, 1H, C(2)H), 4.78 (quin., J 6Hz, 1H, C(3)H), 5.55 (d, J 2.5Hz, 1H, C(5)H). m/e : 213 (M+ —CO, 42%), 200(8), 198 (4), 166 (46), 159 (25), 116 (58), 98 (54), 97 (33), 84 (100).

EXAMPLE 10

(3RS, 5SR)-3-Iodomethyl-4-oxa-1-azabicyclo[3.2.0]heptan-7-one

Pale yellow gum (Found : M+, 252.95982, C$_6$H$_8$NO$_2$I requires 252.96016). $\nu_{max}$ (CHCl$_3$) : 1790 (β-lactam C=O)cm$^{-1}$. δ p.p.m. (CDCl$_3$) : 2.7 – 3.5 (complex, 5H, C(6)H$_2$, C(2)H, CH$_2$I), 4.18 (dd, J 11.5, J' 6Hz, 1H, C(2)H), 4.58 (quin., J 6Hz, 1H, C(3)H), 5.56 (d, J 2.5Hz, 1H, C(5)H). m/e : 253 (M+, 3%), 225 (100), 212 (30), 211 (40), 210 (15), 126 (M+ —I, 75), 98 (70).

EXAMPLE 11

(3RS, 5SR)-3-Acetoxymethyl-4-oxa-1-azabicyclo[3.2.0]heptan-7-one

Colourless gum. $\nu_{max}$ (CHCl$_3$) : 1790 ($\beta$-lactam C=O), 1745 (acetate C=O)cm$^{-1}$. $\delta$ p.p.m. (CDCl$_3$) : 2.17 (s, 3H, COCH$_3$), 2.7 – 3.6 (overlapped m, 3H, C(6)H$_2$ and C(2)H), ca 4.0 (overlapped m, 1H, C(2)H), 4.25 (d, J 5Hz, 2H, CH$_2$OAc), 4.65 (quin., J 5Hz, 1H, C(3)H), 5.48 (br.s, 1H, C(5)H).

EXAMPLE 12

(3RS, 5SR)-3-Formyloxymethyl-4-oxa-1-azabicyclo[3.2.0]-heptan-7-one

Colourless gum. $\nu_{max}$ (CHCl$_3$) : 1790 ($\beta$-lactam C=O), 1735 (formate C=O)cm$^{-1}$. $\delta$ p.p.m. (CDCl$_3$) : 2.7 – 3.1 (complex, 2H, C(6)H, C(2)H), 3.45 (dd, J 16, J' 2.5Hz, 1H, C(6)H), 4.10 (dd, J 11, J' 6.5 Hz, 1H, C(2)H), 4.35 (m, 2H, CH$_2$O), 4.68 (quin., J 6.5Hz, 1H, C(3)H), 5.48 (d, J 2.5Hz, 1H, C(5)H), 8.30 (s, 1H, CHO).

EXAMPLE 13

(3RS, 5SR)-3-Benzoyloxymethyl-4-oxa-1-azabicyclo[3.2.0]-heptan-7-one

Colourless gum. $\nu_{max}$ (CHCl$_3$) : 1783 ($\beta$-lactam C=O), 1720 (benzoate C=O)cm$^{-1}$. $\delta$ p.p.m. (CDCl$_3$) : 2.81 (d, J 16Hz, 1H, C(6)H), 2.89 (dd, J 11, J' 6Hz, 1H, C(2)H), 3.27 (dd, J 16, J' 2Hz, 1H, C(6)H), 4.02 (dd, J 11, J' 6.5Hz, 1H, C(2)H), 4.47 (d, J 4Hz, 2H, CH$_2$O), 4.66 (m, 1H, C(3)H), 5.34 (d, J 2Hz, 1H, C(5)H), 7.25 – 7.60 (m, 3H, Ar-H), 7.95 (dd, J 8, J' 2Hz, 2H, Ar-H). m/e : 219 (M$^+$ —CO, 35%), 204 (31), 190 (14), 179 (15), 152 (12), 142 (13), 105 (100).

EXAMPLE 14

(3RS, 5SR)-3-p-Nitrobenzoyloxymethyl-4-oxa-1-azabicyclo[3.2.0]heptan-7-one

Colourless prisms (from diethyl ether), m.p. 113°–114° (Found : C, 53.64; H, 4.38; N, 9.29. C$_{13}$H$_{12}$N$_2$O$_6$ requires C, 53.43; H, 4.14; N, 9.59%). $\nu_{max}$ (CHCl$_3$) : 1780 ($\beta$-lactam C=O), 1720 (ester C=O), 1525 and 1340 (aromatic NO$_2$)cm$^{-1}$. $\delta$ p.p.m. (CDCl$_3$) : 2.80 (d, J 16Hz, 1H, C(6)H), 2.88 (dd, J 11, J' 5.5 Hz, 1H, C(2)H), 3.32 (dd, J 16, J' 2Hz, 1H, C(6)H), 4.00 (dd, J 11, J' 6Hz, 1H, C(2)H), 4.35 (d, J 4Hz, 2H, CH$_2$O), 4.60 (m, 1H, C(3)H), 5.43 (d, J 2Hz, 1H, C(5)H), 8.20 (s, 4H, Ar-H). m/e : 264 (M$^+$ —CO, 12%), 251 (5), 249 (5), 204 (4), 150 (100).

EXAMPLE 15

(3RS, 5SR)-3-p-Nitrophenoxymethyl-4-oxa-1-azabicyclo[3.2.0]heptan-7-one

Colourless gum. $\nu_{max}$ (CHCl$_3$) : 1780 ($\beta$-lactam C=O), 1610, 1595, 1500 (aromatic C=C), 1515 and 1345 (aromatic NO$_2$)cm$^{-1}$. $\delta$ p.p.m. (CDCl$_3$): 2.8 – 3.7 (complex, 3H, C(6)H, C(2)H), 4.0 – 4.4 (complex, 3H, C(2)H, CH$_2$O), 4.86 (m, 1H, C(3)H), 5.60 (d, J 2Hz, 1H, C(5)H), 7.22 (d, J 8Hz, 2H, Ar-H), 8.48 (d, J 8Hz, 2H, Ar-H).

EXAMPLE 16

(3RS, 5SR)-3-Phthalimidomethyl-4-oxa-1-azabicyclo[3.2.0]-heptan-7-one

Colourless needles (from ethyl acetate/petroleum ether, b.p. 60°–80°), m.p. 137°–138° (Found : C, 61.85; H, 4.69; N, 10.07. C$_{14}$H$_{12}$N$_2$O$_4$ requires C, 61.76; H, 4.44; N, 10.29%). $\nu_{max}$ (CHCl$_3$) : 1785 ($\beta$-lactam C=O), 1720 (phthalimido C=O)cm$^{-1}$ $\delta$ p.p.m. (CDCl$_3$) : 2.7 – 3.1 (complex, 2H, C(6)H, C(2)H), 3.38 (dd, J 16, J' 2.5 Hz, 1H, C(6)H), 3.7 – 4.3 (complex, 3H, C(2)H, CH$_2$N), 4.75 (quin., J 6Hz, 1H, C(3)H), 5.51 (d, J 2.5Hz, 1H, C(5)H), 7.75 – 8.15 (m, 4H, Ar-H).

EXAMPLE 17

(3RS, 5SR)-3-Azidomethyl-4-oxa-1-azabicyclo[3.2.0]heptan-7-one

Colourless gum. $\nu_{max}$ (CHCl$_3$) : 2100 (azide N$_3$), 1785 ($\beta$-lactam C=O)cm$^{-1}$. $\delta$ p.p.m. (CDCl$_3$) ; 2.6 – 3.6 (complex, 5H, C(6)H$_2$, C(2)H, CH$_2$N$_3$), 4.02 (dd, J 10.5, J' 7Hz, 1H, C(2)H), 4.50 (m, 1H, C(3)H), 5.53 (d, J 2.5Hz, 1H, C(5)H). m/e : 169 (M$^+$ + H, 2%), 141 (10), 140 (M$^+$ —CO, 100), 127 (30), 126 (23), 112 (45), 70 (94).

EXAMPLE 18

(3RS, 5RS)-3-Formyloxymethyl-4-oxa-1-azabicyclo[3.2.0]-heptan-7-one

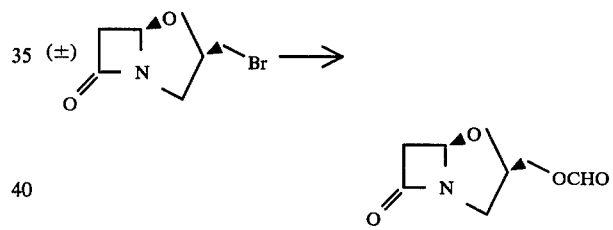

(3RS, 5RS)-3-Bromomethyl-4-oxa-1-azabicyclo[3.2.0]-heptan-7-one was converted into the title compound using the process described for Example 12. The title compound was obtained as a colourless gum (12% yield). $\nu_{max}$(CHCl$_3$) : 1790 ($\beta$-lactam C=O), 1735 (formate C=O)cm$^{-1}$. $\delta$ p.p.m. (CDCl$_3$) 2.8 – 4.0 (complex, 4H, C(6)H$_2$, C(2)H$_2$), 4.38 (d, J 4.5 Hz, 2H, CH$_2$O), 4.70 (m, 1H, C(3)H), 5.32 (br.s, 1H, C(5)H), 8.27 (s, 1H CHO).

EXAMPLE 19

(3RS, 5SR)-3-Phenylsulphonylmethyl-4-oxa-1-azabicyclo[3.2.0]-heptan-7-one and (3RS, 5SR)-3-phenylsulphinylmethyl-4-oxa-1-azabicyclo[3.2.0]heptan-7-one

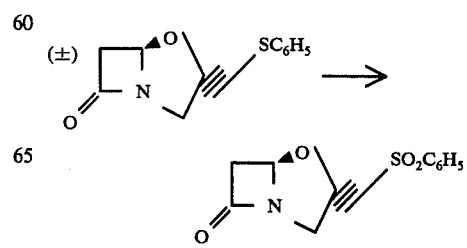

-continued

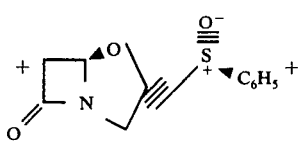

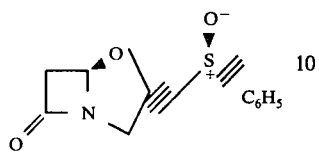

(3RS, 5SR)-3Phenylthiomethyl-4-oxa-1-azabicyclo[3.2.0] heptan-7-one (200 mg) was dissolved in dry methylene chloride (5 ml) and the solution was stirred and ice-cooled while a solution of m-chloroperbenzoic acid (90% pure; 200 mg) in dry methylene chloride (2 ml) was added dropwise. After addition was complete, the solution was stirred and ice-cooled for 30 minutes and was then diluted with ethyl acetate (50 ml). The solution was washed with sodium bicarbonate solution, water, and saturated brine. The solution was dried and the solvent removed to yield a colourless crystalline solid (200 mg). The crude product was chromatographed on silica gel (15 g) using ethyl acetate/petroleum ether to give the sulphone (80 mg) and the two separated isomers of the sulphoxide (50 mg each).

The sulphone, on recrystallisation from ethyl acetate, was obtained as colourless needles, m.p. 153°–154°. (Found, C, 53.75; H, 4.99; N, 5.22. $C_{12}H_{13}NO_4S$ requires C, 53.92; H, 4.90; N, 5.24%). $\nu_{max}$(CHCl$_3$) : 1785 ($\beta$-lactam C=O), 1150 (sulphone S=O)cm$^{-1}$ . $\delta$ p.p.m. (CDCl$_3$) : 2.7 – 3.9 [complex, 5H, C(6)H, C(2)H, CH$_2$SO$_2$Ph]; 4.21 [dd, J 11.5Hz, J' 6.5Hz, C(2)H]; 4.72 [quin., J 6.5 Hz, 1H, C(3)H]; 5.40 [d, J 2Hz, 1H C(5)H]; 7.70 – 8.25 (m 5H, $C_6H_5$).

The sulphoxide (isomer I), on recrystallisation from ethyl acetate, was obtained as fine colourless needles, m.p. 148°–148.5° (Found C, 57.42; H, 5.49; N, 5.41; $C_{12}H_{13}NO_3S$ requires C, 57.36; H, 5.22; N, 5.58%). $\nu_{max}$ (CHCl$_3$) : 1790 ($\beta$-lactam C=O), 1040 (sulphoxide S→O)cm$^{-1}$. $\delta$ p.p.m. (CDCl$_3$): 2.5 – 3.2 [complex, 4H, C(6)H, C(2)H, CH$_2$SOPh]; 3.46 [dd, J 16Hz, J' 2Hz, 1H, C(6)H]; 4.12 [dd, J 12Hz, J' 6.5Hz, 1H, C(2)H]; 4.89 [quin., J 6.5Hz, 1H, C(3)H]; 5.52 [d, J 2Hz, 1H C(5)H]; 7.76 (br.s, 5H, $C_6H_5$).

The sulphoxide (isomer II), on recrystallisation from ethyl acetate/petroleum ether, was obtained as colourless prisms, m.p. 115°–115.5° (Found C, 57.17; H, 5.36; N, 5.29; $C_{12}H_{13}NO_3S$ requires C, 57.37; H, 5.22; N, 5.58%) $\nu_{max}$ (CHCl$_3$) : 1785 ($\beta$-lactam C=O), 1040 (sulphoxide S→O)cm$^{-1}$. $\delta$ p.p.m. (CDCl$_3$) : 2.7 – 3.6 [complex, 5H, C(6)H$_2$, C(2)H, CH$_2$SOPh]; 4.12 [dd, J 11Hz, J' 6Hz, 1H, C(2)H]; 4.45 [quin., J 6Hz, 1H, C(3)H]; 5.50 [d, J 2Hz, 1H, C(5)H]; 7.70 [br.s, 5H, $C_6H_5$].

EXAMPLE 20

(3RS, 5SR)-3-p-Nitrophenylsulphonylmethyl-4-oxa-1-azabicyclo[3.2.0] heptan-7-one and (3RS, 5SR)-3-p-Nitrophenylsulphinylmethyl-4-oxa-1-azabicyclo[3.2.0] heptan-7-one

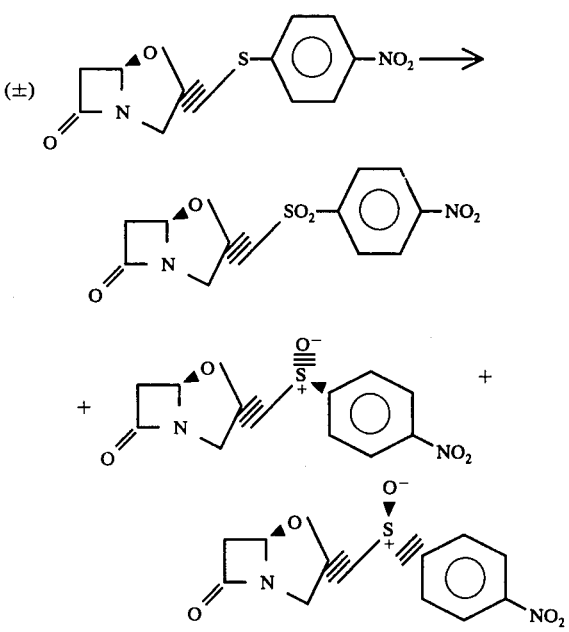

(3RS, 5SR)-3-p-Nitropheylthiomethyl-4-oxa-1-azabicyclo[3.2.0] heptan-7-one (80 mg) was converted into the title compounds using the process described in Example 19. The sulphone was obtained as colourless crystals, m.p. 134° – 137° (18 mg., 20%), one sulphoxide isomer was obtained as colourless crystals, m.p. 163° – 166° (20 mg., 24%), and the other sulphoxide isomer was obtained as a colourless gum (20 mg, 24%).

The sulphone had $\nu_{max}$ (CHCl$_3$) : 1790 ($\beta$-lactam C=O), 1535 and 1345 (aromatic NO$_2$), 1150 (sulphone)cm$^{-1}$; $\delta$ p.p.m. (CDCl$_3$) : 2.6 – 2.9 (m, 2H, C(6)H, C(2)H), 3.15 – 3.50 (m, 3H, C(6)H, CH$_2$SO$_2$), 4.11 (dd, J 12, J' 6Hz, 1H, C(2)H), 4.62 (m, 1H, C(3)H), 5.15 (d, J 2Hz, 1H, C(5)H), 8.05 (d, J 9Hz, 2H, Ar-H), 8.34 (d, J 9Hz, 2H, Ar-H); m/e : 284 (M$^+$ −CO, 42%), 271 (26), 196 (13), 126 (26), 123 (20), 122 (22), 98 (100).

The sulphoxide (isomer I, m.p. 163°–166°) had $\nu_{max}$ (CHCl$_3$) : 1783 ($\beta$-lactam C=O), 1525 and 1340 (aromatic NO$_2$), 1040 (sulphoxide)cm$^{-1}$; $\delta$ p.p.m. (CDCl$_3$) : 2.65 (dd, J 11, J' 6Hz, 1H, C(2)H), 2.76 (d, J 16Hz, 1H, C(6)H), 2.97 (d, J 6Hz, 2H, CH$_2$SO), 3.33 (dd, J 16, J' 2.5 Hz, 1H, C(6)H), 4.05 (dd, J 11, J' 6Hz, 1H, C(2)H) 4.75 (quin., J 6Hz, 1H, C(3)H), 5.35 (d, J 2.5 Hz, 1H, C(5)H), 7.78 (d, J 9Hz, 2H, Ar-H), 8.33 (d, J 9Hz, 2H, Ar-H).

The sulphoxide (isomer II, gum) had $\nu_{max}$ (CHCl$_3$) : 1785 ($\beta$-lactam C=O), 1525 and 1340 (aromatic NO$_2$), 1035 (sulphoxide)cm$^{-1}$ ; $\delta$ p.p.m. (CDCl$_3$) 2.65 – 3.40 (complex, 3H, C(6)H$_2$, C(2)H), 3.13 (d, J 5.5hz, 2H, CH$_2$SO), 4.05 (dd, J 11, J' 6Hz, 1H C(2)H), 4.45 (m, 1H, C(3)H), 5.31 (d, J 2Hz, 1H, C(5)H), 7.77 (d, J 9Hz, 2H, Ar-H), 8.31 (d, J 9Hz, 2H, Ar-H).

EXAMPLE 21

(3RS, 5SR)-3-Hydroxymethyl-4-oxa-1-azabicyclo[3.2.0]-heptan-7-one

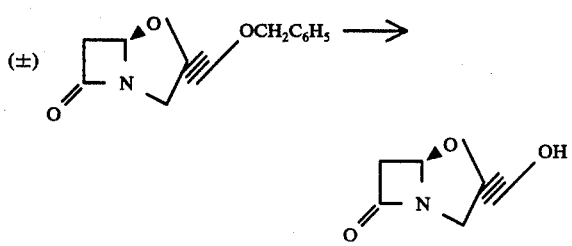

(3RS, 5SR)-3-Benzyloxymethyl-4-oxa-1-azabicyclo-[3.2.0] heptan-7-one (120 mg) was dissolved in 95% ethanol (10 ml) and the solution was shaken with 10% palladium-on-charcoal (80 mg) under one atmosphere of hydrogen at room temperature for 6 hours. The catalyst was removed by filtration and was washed with ethanol. The solvent was removed from the combined filtrate and washings to yield a colourless gum (75 mg). The gum was chromatographed on silica gel (10 g) using ethyl acetate/petroleum ether (b.p. 60°–80°) to give the title compound as a colourless oil (12 mg). $\nu_{max}$ (CHCl$_3$) : 3380 (OH), 1785 ($\beta$-lactam C=O)cm$^{-1}$. $\delta$ p.p.m. (CDCl$_3$) 2.05 (br.s, 1H, OH), 2.81 (d, J 16Hz, 1H, C(6)H), 2.88 (dd, J 11, J' 6.5Hz, 1H, C(2)H), 3.29 (dd, J 16, J' 2Hz, 1H, C(6)H), 3.45 – 3.85 (m, 2H, CH$_2$O), 3.92 (dd, J 11, J' 7Hz, 1H, C(2)H), 4.40 (m, 1H, C(3)H), 5.33 (d, J 2Hz, 1H, C(5)H).

EXAMPLE 22

(3RS, 5SR)-3-(N-Phenylcarbamoyloxymethyl)-4-oxa-1-azabicyclo[3.2.0]heptan-7-one

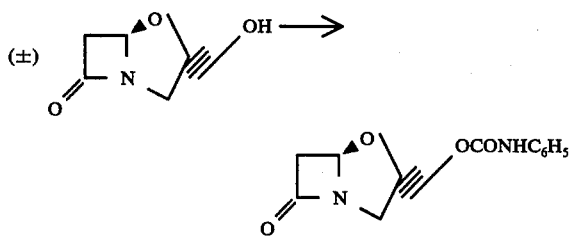

(3RS, 5SR)-3-Hydroxymethyl-4-oxa-1-azabicyclo[3.2.0]heptan-7-one (12 mg) was dissolved in 1,2-dimethoxyethane (0.5 ml) containings a trace of dry pyridine. Phenyl isocyanate (15 mg) was added to the solution which was then kept at room temperature with exclusion of moisture for 3 days. The mixture diluted with ethyl acetate (20 ml) and washed once with water (10 ml). The solution was dried and the solvent removed to yield a colourless solid. The crude product was chromatographed on silica gel (10 g) using ethyl acetate/petroleum ether (b.p. 60° –80°) to give the title compound as colourless prisms (15 mg., 68% yield). $\nu_{max}$(CHCl$_3$) : 3350, 3170 (NH), 1780 ($\beta$-lactam C=O), 1735 (urethane C=O), 1600 (aromatic C=C), 1520 (amide II)cm$^{-1}$. $\delta$ p.p.m. (CDCl$_3$) : 2.75 (d, J 16Hz, 1H, C(6)H), 2.78 (dd, J 11, J' 6Hz, 1H, C(2)H), 3.27 (dd, J 16, J' 2Hz, 1H, C(6)H), 3.95 (dd, J 11, J' 6Hz, 1H, C(2)H), 4.19 (d, J 4.5 Hz, 2H, CH$_2$O), 4.45 (m, 1H, C(3)H), 5.43 (d, J 2Hz, 1H, C(5)H), 6.90 (br.s, 1H, NH), 7.2 – 7.5 (complex, 5H, Ar-H).

EXAMPLE 23

(3RS, 5RS)- and (3RS, 5SR)-3-(2-o-Nitrophenylselenoethyl)-4-oxa-1-azabicyclo-[3.2.0]heptan-7-one The following reaction sequence was conducted under a dry nitrogen atomosphere with exclusion of moisture throughout.

o-Nitrophenylseleno cyanide (130 mg., 0.6mmole) was dissolved in dry 1,2-dimethoxyethane and the solution was stirred and ice-cooled while sodium borohydride (23 mg., 0.6 mmole) was added. The cooling bath was removed and stirring was continued for 10 minutes. Methanol (ca 20 mg.) was added, the mixture was stirred for 3 minutes, and was then ice-cooled and stirred while a solution of 3-(2-bromoethyl)-4-oxa-1-azabicyclo[3.2.0]heptan-7-one (mixture of two isomers) (110 mg., 0.5mmole) in dry dimethylformamide (3 ml) was added dropwise. After addition was complete, the cooling bath was removed and stirring was continued for 16 hours. The mixture was diluted with ethyl acetate (50 ml) and was washed three times with water (20 ml portions). The solution was dried and the solvent was removed to yield a bright yellow gum. The gum was chromatographed on silica gel (15 g) using ethyl acetate/petroleum ether (b.p. 60°-80°) to give the mixture of title compounds as a bright yellow gum (140 mg., 82% yield).

The mixture was rechromatographed on silica gel (10 g) to give samples of the two pure title compounds, both as yellow gums. The less polar isomer had $\nu_{max}$(CHCl$_3$) : 1780 ($\beta$-lactam C=O), 1510 and 1330 (aromatic NO$_2$)cm$^{-1}$; $\delta$ p.p.m. (CDCl$_3$) : 1.75 – 2.05 (m, 2H, CH$_2$), 2.4 – 3.3 (complex, 5H, C(6)H$_2$, C(2)H, CH$_2$Se), 3.81 (dd, J 10.5, J' 6Hz, 1H, C(2)H), 4.18 (quin, J 6Hz, 1H, C(3)H), 5.28 (d, J 2Hz, 1H, C(5)H), 7.1 – 7.5 (m, 3H, Ar-H), 8.16 (d, J 7Hz, 1H, Ar-H). The more polar isomer had $\nu_{max}$(CHCl$_3$) : 1780 ($\beta$-lactam C=O), 1510 and 1330 (aromatic NO$_2$)cm$^{-1}$; $\delta$p.p.m. (CDCl$_3$) : 1.75 – 2.05 (m, 2H, CH$_2$) 2.4 – 3.3 (complex, 6H, C(6)H$_2$, C(2)H$_2$, CH$_2$Se), 4.23 (quin., J 6Hz, 1H, C(3)H), 4.97 (d, J 2Hz, 1H, C(5)H), 7.10 – 7.50 (m, 3H, Ar-H), 8.17 (d, J 7Hz, 1H, Ar-H).

EXAMPLE 24

(3RS, 5RS)- and (3RS, 5SR)-3-Vinyl-4-oxa-1-azabicyclo[3.2.0]heptan-7-one

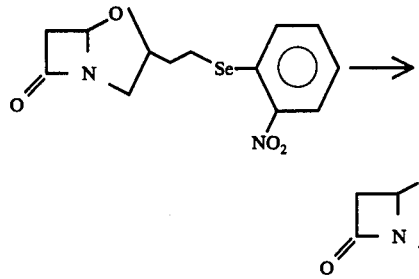

3-(2-o-Nitrophenylselenoethyl)4-oxa-1-azabicyclo[3.2.0]-heptan-7-one (mixture of two isomers) (500 mg., 1.46 mmole) was dissolved in 1,2-dimethoxyethane (15 ml) and the solution was stirred and ice-cooled while 30% w/v hydrogen peroxide (1.5 ml) was added dropwise. After addition, the cooling bath was removed and stirring was continued for 17 hours. The mixture was diluted with ethyl acetate (100 ml) and was washed twice with saturated sodium bicarbonate solution and once with saturated brine. The solution was dried and the solvent was removed to yield a yellow gum. The gum was chromatographed on silica gel (25 g) using ethyl acetate/petroleum ether (b.p. 60°-80°) to give the less polar isomer of the title compound as a colourless oil (65 mg., 32%) and the more polar isomer also as a colourless oil (80 mg., 39%).

The less polar isomer had $\nu_{max}$(CHCl$_3$) : 1780 ($\beta$-lactam C=O)cm$^{-1}$ $\delta$p.p.m. (CDCl$_3$) : 2.64 (dd, J 11, J' 7Hz, 1H, C(2)H), 2.82 (d, J 16Hz, 1H, C(6)H), 3.27 (dd, J 16, J' 2Hz, 1H, C(6)H), 3.96 (dd, J 11, J' 6Hz, 1H, C(2)H), 4.60 (m, 1H, C(3)H), 5.1 - 5.4 (complex, 3H, C(5)H, =CH$_2$), 5.76 (ddd, J 16, J' 9.5, J" 6Hz, 1H, =CH). The more polar isomer had $\nu_{max}$ (CHCl$_3$) : 1780 ($\beta$-lactam C=O)cm$^{-1}$. $\delta$ p.p.m. (CDCl$_3$) : 2.83 (d, J 16 Hz, 1H, C(6)H), 3.05 - 3.55 (complex, 3H, C(6)H, C(2)H$_2$), 4.66 (m, 1H, C(3)H), 5.1 - 5.4 (complex, 3H C(5)H, =CH$_2$), 5.80 (ddd, J 16, J' 9.5, J" 6Hz, 1H, =CH).

EXAMPLE 25

Inhibition of the $\beta$-lactamase from Staphylococcus aureus Russell

The compounds of the invention inhibited the $\beta$-lactamase enzyme produced by Staphylococcus aureus Russell as illustrated in the following Table. I$_{50}$ values were determined using the process described in Belgium Pat. No. 827,926.

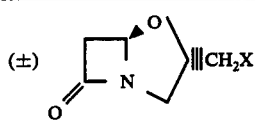

| Preparation in Example No | X | I$_{50}$ ($\mu$g/ml) |
|---|---|---|
| 2.2 | Br | 3.0 |
| 7 | SC$_6$H$_5$ | 2.4 |

-continued

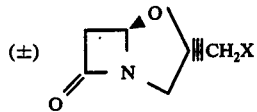

| Preparation in Example No | X | I$_{50}$ ($\mu$g/ml) |
|---|---|---|
| 20 | SO$_2$-C$_6$H$_4$-NO$_2$ | 1.7 |
| 20 | SO-C$_6$H$_4$-NO$_2$ (isomer I, m.p. 163-166°) | 0.8 |
| 15 | O-C$_6$H$_4$-NO$_2$ | 4.4 |
| 22 | OCONHC$_6$H$_5$ | 2.4 |
| 14 | OCO-C$_6$H$_4$-NO$_2$ | 4.4 |

EXAMPLE 26

Antibacterial activity and antibacterial synergy with ampicillin against Staphylococcus aureus Russell Table 1 shows the minimum concentrations of the compounds required to inhibit the growth of Staph. aureus Russell. Table 2 shows the minimum concentrations of ampicillin required to inhibit the growth of Staph. aureus Russell in the presence of the stated concentrations of the compounds of the invention.

Table 1

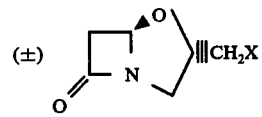

| Preparation in Example No. | X | M.I.C.($\mu$g/ml) |
|---|---|---|
| 19 | SO$_2$C$_6$H$_5$ | 250 |
| 9 | S-C$_6$H$_4$-NO$_2$ | 62 |
| 6.2 | CH$_2$Br (mixture of 2 isomers) | 500 |
| 20 | SO-C$_6$H$_4$-NO$_2$ (isomer I, mp 163-166°) | 31-62 |
| 13 | OCOC$_6$H$_5$ | 250 |

Table 2

| X | Conc. (μg/ml) of inhibitor | M.I.C. (μg/ml) Ampicillin |
|---|---|---|
| No inhibitor | — | 250 |
| $SO_2C_6H_5$ | 20 | 1.25 |
| 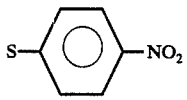 | 5<br>20 | 10<br>0.6 – 1.2 |
| $CH_2Br$ (mixture of 2 isomers) | 20 | 0.4 |
| 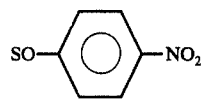<br>(isomer I, m.p. 163–166°) | 5 | 1.25 |
| $OCOC_6H_5$ | 20 | 5 |

EXAMPLE 27

Acute toxicity in mice

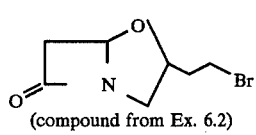

(compound from Ex. 6.2)

The compound (mixture of 2 isomers) from Example 6.2 was tested for acute toxicity in mice as described below.

Mice: CDI, female, 18 – 22 gm. 5 mice per group
Route: Subcutaneous.
Dosage: 2000, 1000, 500, and 250 mg/Kg.

The compound was injected in aqueous dimethylformamide ($\leq 15\%$ DMF) at 0.4 ml/20 g for the 2000 mg./Kg. dosage and at 0.2 ml/20 g. for the other dosages.

Results

| Dosage (mg./Kg.) | Number of mice alive | | | |
|---|---|---|---|---|
| | Days 0 and 1 | Day 2 | Day 3 | Days 4 to 7 |
| 2000 | 5/5 | 3/5 | 2/5 | 2/5 |
| 1000 | 5/5 | 5/5 | 5/5 | 5/5 |
| 500 | 5/5 | 5/5 | 5/5 | 5/5 |
| 250 | 5/5 | 5/5 | 5/5 | 5/5 |

At dosages up to 100 mg./Kg. all mice remained alive and gained in weight over the observation period (7 days). At a dosage of 2000 mg./Kg. three out of the five mice were dead within 3 days, but the other two remained alive and had gained weight by the end of the observation period.

What we claim is:

1. A compound of the formula (I):

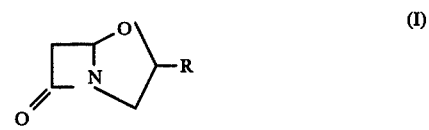

wherein R is hydrogen, alkyl of 1–4 carbon atoms, alkenyl of 2–4 carbon atoms, epoxide of 2–4 carbon atoms or alkyl of 1–4 carbon atoms substituted by one or two moieties selected from the group consisting of halogen, azido and phthalimido.

2. A compound of the formula (II) or (III):

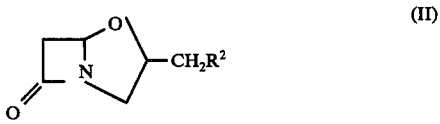

or

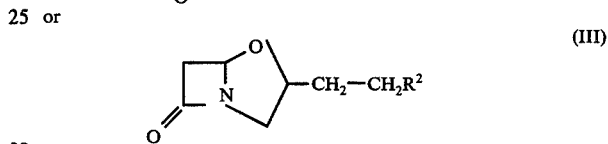

wherein $R^2$ is hydrogen.

3. A compound wherein the compound is of the formula:

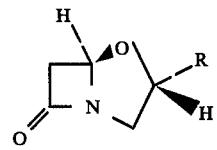

wherein R is hydrogen, alkyl of 1–4 carbon atoms, alkenyl of 2–4 carbon atoms, epoxide of 2–4 carbon atoms or alkyl of 1–4 carbon atoms substituted by one or two moieties selected from the group consisting of halogen, azido and phthalimido.

4. A compound according to claim 1 wherein R is hydrogen, 2-bromoethyl, epoxyethyl, 1,2-dibromoethyl, bromomethyl, iodomethyl, phthalimidomethyl, azidomethyl or vinyl.

5. A compound according to claim 2 wherein $R^2$ is bromine.

* * * * *